United States Patent [19]

Hewett

[11] Patent Number: 4,851,210

[45] Date of Patent: Jul. 25, 1989

[54] BLOOD TYPING DEVICE

[75] Inventor: Gary E. Hewett, Atherton, Calif.

[73] Assignee: Genelabs Incorporated, Redwood City, Calif.

[21] Appl. No.: 866,350

[22] Filed: May 22, 1986

[51] Int. Cl.$^4$ ............................................. G01N 31/00
[52] U.S. Cl. ...................................... 424/11; 210/490; 210/500.29; 210/500.36; 210/500.38; 210/500.42; 422/55; 422/57; 422/60; 435/29; 435/30; 435/34; 436/513; 436/530; 436/531; 436/548
[58] Field of Search ............... 210/488, 490, 492, 506, 210/500.29, 500.36, 500.38, 500.42; 422/55, 57, 60; 435/29, 30, 34; 436/513, 530, 531, 548; 424/11

[56] References Cited

U.S. PATENT DOCUMENTS

| | | | |
|---|---|---|---|
| 4,130,395 | 12/1978 | Chryssanthou | 436/511 |
| 4,250,256 | 2/1981 | Wielinger et al. | 435/32 |
| 4,366,241 | 12/1982 | Tom et al. | 436/807 |
| 4,632,901 | 12/1986 | Valkirs et al. | 436/807 |

Primary Examiner—Robert J. Warden
Assistant Examiner—Stephen C. Wieder
Attorney, Agent, or Firm—Richard L. Neeley

[57] ABSTRACT

A membrane structure is disclosed having controlled capillarity useful in detecting cells in a solution by promoting effective contacting between cells and the membrane surface bearing affinity for selected cell sites. Also disclosed is a mtehod of using such membrane structures to detect particles in solution. One embodiment of the invention is an improved blood-typing device and method. The device may be attached to a blood bag, clamp, stick or the like, to provide a permanent visual record of blood type.

33 Claims, 1 Drawing Sheet

BLOOD TYPING DEVICE

FIELD OF THE INVENTION

The present invention relates to a membrane structure having controlled capillarity that allows the contacting of cells in an absorbed solution with the membrane surface. This contacting permits effective binding by cells to affinity regions on the membrane surface. More specifically, the present invention relates to a system and method of blood typing, based on immunospecific binding of blood cells to a microporous membrane and support.

BACKGROUND OF THE INVENTION

Affinity surface detection of cells requires the effective binding of the cells to specific binding regions on the surface. Affinity regions such as antibodies specific for antigenic regions on cells have long been known. However, the detection by the affinity surface has a serious mechanical problem, the difficulty of rapid effective binding between the affinity region and the cell, which may be in comparatively low concentration in the solution. Even more serious is the problem when the cell to be detected is fragile, such as a red blood cell (RBC). If the contacting or the conditions are such that the RBC ruptures, then detection may be impossible due to non-specific coloring. Even for other cells, the lysis of RBC in a solution often so colors the detection device so as to make the assay non-functional. Therefore, the ability to detect a cell in solution, without contacting with force sufficient to lyse cells or conditions that cause cell damage, offers a significant improvement in detection technologies. Another problem with too great a contacting force is non-specific binding. Therefore, even if the cells fail to lyse, the binding could be non-specific if excessively strong capillarity is present.

Blood Cell Detection

One common set of detection devices is adapted to determine blood type. It is essential in supplying blood from a donor to a recipient to match the two blood types, to ensure that the recipient does not have a severe immunological response to the donor's blood. Such a response can occur when the recipient has antibodies, or can develop antibodies, to the surface antigens of the donor's blood cells.

The most important of cell antigens, for blood-compatibility purposes, are the A and B antigens, which form the basis of the four major cell types among humans: type O (neither antigen), type A (A antigen), type B (B antigen), and AB (both antigens). The serum of the individuals of each cell type normally contains antibodies directed against the A and/or B antigens which are not present on the individuals's blood cells. That is, type O individuals have both anti-A and anti-B antibodies, type B individuals have anti-A antibodies only, and so on. To prevent the undesired immune response, it is necesary that donor blood cells not contain either A or B antigents for which the recipient has the corresponding antibodies.

Another important antigen group which is matched is the Rh group, associated with D antigens on red blood cells. If an Rh(−) individual, whose red blood cells lack the D antigen group is given blood from an Rh(+) donor, an immune response against the foreign antigen leads to anti-D antibodies which can react with the foreign cells, particularly if a second, later transfusion of Rh(+) blood is given.

Antibodies for several other antigen groups, such as human leukocytic antigens (HLA), are also capable of determination using this system. This is a crossmatching procedure for secondary blood antigen groups and it is only appropriate when individuals are receiving chronic transfusions or other continuous exposure to such secondary antigens.

In the usual blood-banking operation, donor blood is initially screened for A, B, and Rh type and for selected secondary antigens. Cell typing for major blood type is carried out most commonly by cell agglutination methods in which the donor blood cells are incubated with reagent anti-A and anti-B antibodies, to determine the presence of A and/or B surface antigens. Depending on the agglutination pattern, the blood can be typed as O, A, B, or AB. A similar agglutination test is used to test for Rh factor. The blood type can be confirmed by showing the ability of the donor serum, which lacks the antigen-type antibody, to agglutinate reagent red blood cells of a defined blood group.

Agglutination testing procedures commonly used in blood typing are susceptible to several types of technical and clerical errors in the testing procedure. The technician may inadvertently add the wrong reagent or blood sample to the assay mixture, or misread the agglutination result. Clerical errors can arise in transferring the blood agglutination results to the appropriate blood containers. These types of technical and clerical errors are especially difficult to avoid where hundreds of samples are being handled on a daily basis, as is common in blood banks.

Because of the possibility of such error, and the importance of correctly matching donor and recipient blood types, present blood donor systems include a number of backup checks to confirm major blood type. As already noted, the intial blood typing involves agglutination of donor cells, and confirmation of the blood type by serum agglutination of reagent cells of known type. Before the blood leaves the blood bank, the major blood type groups—O, A, B, AB, and Rh—are confirmed by repeating the initial assay. The major blood groups are checked again when the donor blood is received by the hospital or clinic. The duplication needed to ensure correct donor blood type is relatively costly and time consuming both to the blood bank supplying the blood and to the receiving facility.

Cell typing methods which rely on immunospecific cell binding to a solid surface coated with cell-type specific antibodies have also been proposed. In one method, blood cells are first digested with hydrolytic enzyme, to remove surface groups which interfere with cell binding to surface-bound antibodies. The enzyme-treated cells are washed, diluted, added to microtiter wells coated with selected anti-blood group antibodies, and the microtiter plates are centrifuged to force the cells against the antibody-coated surface in each well. A positive reaction produces a monolayer of cells on the coated portion of the well surface, and a negative reaction, a discrete cell-pellet at the bottom of the well. The presence of the cell monolayer is established by reading the absorption of a monochromatic light beam at 405 nm through the monolayer region of the well outside the region of the pelleted cells. (Sinor, L. T., et al., *Transfusion* (1985) 25: 21).

Another solid-phase method is disclosed in U.S. Pat. No. 4,275,053. A solid-phase support used in the method is prepared by irreversibly attaching cells having a selected cell-surface antigen type to a support matrix, then binding antigen-specific antibodies to the attached cells. In the presence of a blood sample having the selected surface antigen, the antibodies bind the suspended cells in the sample, forming a monolayer of analyte cells which are detected by standard instrumentation procedures, such as densitometric scanning. Europeant patent application No. 84106844 (Pub. No. 130,434) discloses the use of monoclonal antibodies in a solid lacquered film specific for blood group antigens. Other blood typing patents or publications are: U.S. Pat. Nos. 2,770,572; 4,200,690; 4,246,339; and 4,407,943; PCT W085/01354; and European patent application No. 81108009 (Pub. No. 51,748).

Many of the methods previously used for detecting blood types required the use of centrifugation to facilitate pelleting and contacting of blood cells with antibody. Such a step requires complex centrifuge equipment and further increases the possibility of errors occuring during the blood typing process. In addition, such blood typing processes are slow and require significant technical training to determine blood type.

The solid-phase blood typing methods have limited reliability, due to the weak color reaction of a monolayer of cells on a solid surface. Also, since the monolayer of cells cannot conveniently be preserved in a dehydrated form suitable for instrument analysis, the only way to confirm the original blood-group typing is to rerun the assay. The present invention solves the problems of weak color reaction, ease of use, and convenient storage by employing a dry or nearly dry membrane structure embodying a water-permeable, noncell disruptive membrane that wicks the aqueous phase into a hydrophilic matrix thereby efficiently contacting the exposed antibodies with red blood cells.

SUMMARY OF THE INVENTION

Described is a novel method of preparing a membrane structure having controlled capillarity for use in the detection of cells in a solution by effective contacting of the cells with affinity regions on the membrane structure. The membrane surface excludes the cells from penetrating into the interior.

One application of this method provides a blood typing system which largely eliminates the possibility of technical or clerical errors, and with it, the need for multiple checks on blood type. This blood typing system comprises a dry membrane structure, which when contacted with a liquid containing blood cells, wicks the liquid into a wetable, water-permeable matrix causing firm contact between the blood cells and type specific antibody bound to the membrane. This dry membrane structure provides a membrane surface in combination with a water-permeable wicking material, that by controlled capillarity or absorbing action literally sucks or wicks aqueous phase material into the membrane thereby efficiently contacting the cells with specific antibody, without either disrupting the cells or trapping cells non-specifically.

DETAILED DESCRIPTION OF THE INVENTION

Figure 1:
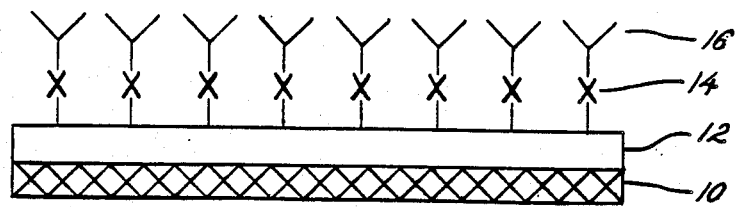
FIG. 1 illustrates an indicator membranesupport construct containing a solid support (10), a microporous, water-permeable, non-cell disruptive membrane surface and interior region treated to have controlled capillarity associated with the membrane surface (12), an optical spacer (14), and type specific antibody (16).

A dry or nearly dry membrane detector system with controlled capillarity is described, with an example of adapting the membrane system for typing blood. Methods of using such blood typing systems to determine human ABO and Rh type are illustrated.

1. Controlled Capillarity

Membrane detector devices require controlled capillarity for proper function. Absorbant porous materials are modified to produce a material having controlled capillarity through a two step process. The first step is to select a base membrane that exhibits a moderately hydrophilic character, that is, one that will draw liquid in at a moderate rate. The second step is the coating of the membrane with chemical agents that effectively control the capillary action of the base membrane materials. One example of such coating agents is polymers which make the base membrane slightly more hydrophobic, thereby controlling capillarity. While many polymers with such properties are anticipated for use as coating materials, preferred are proteins, such as serum albumin, or organic polymers, such as polyvinylalcohol (PVA) and polyvinylpyrolidine (PVP). These coating materials are dissolved in water and applied at a concentration sufficient to result in controlled capillarity of the porous absorbing material. The volume of the coating solution must be sufficient to cause even distribution of the polymer, salt and surfactants throughout the absorbing membrane material without an excess that could dry, cake, crust, or in any other way interfere with the uniform absorption or wicking by capillary action of liquid into the porous material.

Along with the polymer, the coating solution contains salt and surfactants. The salt concentration must be at or slightly below that of isotonic saline. It may be a sodium, potassium, calcium, or other salt that will not cause the rupture of cell membranes by excessively rapid water uptake. Upon hydration of the membrane water is taken up or wicked into the membrane leaving a nearly isotonic environment within the membrane volume.

Surfactants are incorporated into the coating solution to promote uniform coating of the membrane surface and the porous interior without the detrimental buildup of salts or dissolved materials in localized regions. While any surfactant may be used, a preferred surfactant is Tween 20 (Sigma Chemical Co.) at a 0.01 to 1% solution, with a most preferred concentration of 0.1% vol/vol, with salt and polymer as additional ingredients.

The proper concentration of polymer in the coating solution to create controlled capillarity was determined for Bovine Serum Albumin (BSA), polyvinylpyrolidine (PVP), and for polyvinylalcohol (PVA). Solutions of from 5 to 30% BSA (w/v) were formulated and 2 to 20 $\mu$l of each solution applied to 6 mm×6 mm membranes (Immobilon TM). The optional BSA concentration for coating was 17% and 4 $\mu$l was applied. For PVP solutions containing from 10 to 40% were applied to 6 mm×6 mm membranes (Immobilon TM). Samples of 2 to 20 $\mu$l were applied to each surface with optimal coating at 25% PVP and a 4 $\mu$l volume. For PVA, solutions of from 3 to 20% were prepared and applied to 6 mm×6 mm membranes (Immobilon TM). Samples applied varied from 2 to 20 $\mu$l of solution. The optimum coatiang occurred at 12% PVA and 4 $\mu$l per membrane.

Salt in the coatiang solution can be any noninterfering salt, but preferably sodium or potassium chloride. The concentration is isotonic or slightly below isotonic. The surfactant is applied as part of the coating solution to promote coating of the membrane surface and the porous interior of the membrane (or other porous material). Use of surfactant promotes even distribution of polymer and salt throughout the membrane surface and interior without creating buildup or crusting of the coating materials.

In use, the coating solution, containing polymer, salt and surfactant is applied after the affinity ligand (antibody, antigen, hormone, receptor, protein, etc.) has been bound to the membrane. The volume of coating solution should just fill the internal volume of the absorbing materials. In one example the membrane was 6 mm×6 mm×140$\mu$ and the internal volume was 70% void, coatiang required a volume of approximately 4 $\mu$l to produce proper distribution of the dissolved polymer, salt and surfactant. For each new membrane design, the actual quantity required can be determined by applying the solution in increasing quantities until it is no longer completely absorbed.

2. The Assay System for ABO Blood Test

A. Preparing the Membrane Structure

The membrane structure in the blood assay system is composed of a substrate having surface-attached antibodies specific against a selected red blood cell surface antigen.

The substrate used in preparing the membrane structure is one which allows (a) wicking of the liquid phase into the membrane structure; (b) attachment of the antigen-specific antibodies to the substrate surface, (c) immunospecific bidning of red blood cells to the attached antibodies, and (d) modulation of the rate of water absorption by the membrane structure by varying the salt, non-specific protein concentration or charge of the membrane matrix. A variety of materials, including many polymers and glass, are suitable for the support structure of the membrane. Representative polymer materials include latex, polycarbonate, polyvinyldifloride (PVDF), cellulose, nylon, polyvinylacetate, polystyrene, and polyethylene. The membrane substrate material is preferably a sheet or membrane that can be cut in small patches or pads, such as 2-8 mm disks, squares, etd., although other substrate forms, such as beads or rods, may be employed, as will be appreciated below. The substrate may provide, or be modified to provide, surface chemical groups, such as carboxyl, hydroxyl, aldehyde, sulfhydryl, amide, or amine groups, which can participate in covalent chemical linkages used in attaching the antibody to the support. Similarly, linkages may also be through ether bonds. One preferred substrate material used in preparing the supports described in examples I-IV is a chemically activated hydrophilic microporous membrane to which antibodies can be covalently attached such as Immobilon TM by Millipore Corporation.

The base membrane material of the Immobilon TM membrane is a non-interactive fluorocarbon polymer. However, any membrane that excludes the penetration of cells and that allows immobilization of proteins or other affinity agents while retaining native activity will be sufficient. The pore sizes of the Immobilon TM membranes range from 0.65 $\mu$m to 5 $\mu$m.

The hydrophilic microporous membrane must be adjusted to absorb the aqueous phase at a proper rate that is controlled by capillarity. The rate of absorption is controlled by the addition of salts such as potassium or sodium, and by the addition of non-specific polymers. Surface charge or pH may also effect binding. If the rate of water absorption is so high it results in non-specific binding of cells or cell rupture, then the non-specific polymer is increased, thereby decreasiang the rate of water absorption.

The preferred temperature for running a determination of blood groups is room temperature ±5°. However, in the presence of blood rich in lipid components, the optimum temperature may be higher, in the range of 30°-40° C. or more. The elevated temperature is required due to the increased viscosity of the blood fraction caused by the lipid phase.

Among the types of affinity regions are any ligand/ligand receptor, such as antibody-antigen, hormone-receptor, enzyme-substrate, or any two molecular means having binding affinities to one another, with one means in solution and the other means attached to the membrane, thereby facilitating detectable isolation of the cells in the solution.

The cell-specific antibodies attached to the substrate are commonly mouse or human IgM or IgG antibodies which are specific against selected human red cell antigens, and particularly the A, B, and D cell antigens associated with A, B, and Rh(+) human blood groups. Mouse and human IgM antibodies specific against human blood groups A, B groups are available commercially, either as partially purified antisera or in purified form. Anti-D antiserum or monoclonal antibodies for binding to Rh-associated antigens, can also be obtained commercially, and the anti-D antibody can be further purified by known methods. The antibodies may be either polyclonal or monoclonal.

Attachment of antibodies may be accomplished by the use of coupling such as glutaraldehyde, carbonyldimidazole, or trichlorotriazine by methods well-known in the art.

Bethell, G. S., Ayers, J. S., Hancock, W. S. and Hearn, M. T. W. (1979) *J. Biol. Chem.* 254: 2572-2574.

Zuk, R. F., Ginsberg, V. K., Houts, T., Rabble, J., Merrick, H., Ullman, E. F., Fisher, M. M., Sizto, C. C., Stiso, S. N., Littman, D. J. (1985) *Clin. Chem.* 31: 1144-1150.

In a typical procedure, the antibody protein is covalently coupled to the membrane substrate through reactive chemical groups on the substrate surface. The coupling may involve direct chemical bonding between a reactive surface group, such as an aldehyde group, and a suitable protein group, such as primary amines, or may involve cross-linking by means of a suitable bifunctional linking reagent, such as glutaraldehyde. A variety of known coupling reactions are available. Alternatively, for some substrate materials, the secondary antibodies can ba absorbed tightly to the substrate without covalent attachment. In either method, the substrate is washed thoroughly after the binding reaction to remove unbound material. After washing to remove unbound antibody material, the remaining active protein binding sites can be blocked by the addition of other proteinaceous or polymeric material. This protein or polymer material binds to those coupling sites that are not occupied by antibody, thereby reducing or eliminating the non-specific binding of proteins in the test material. One such group of proteins are the non-immunoglobulin components of serum such as alpha-2-macroglobulin and albumin. These proteins may accompany the antibody to complete the binding and blocking reactions simultaneously. Another protein useful for such blocking is the milk protein casein or any other protein that has no affinity for the antigen to be detected.

The membrane material itself may be water absorbing, such as the material Immobilon TM or it can be the membrane in combination with any water-absorbing material such as paper or a hydrophylic polymer. One preferred method of assembling the membrane and the support element is to first bind the membrane component to the support component by the use of a double-sided adhesive, followed by the binding of the specific antibody and adjustment of the membrane to absorb water at the rate appropriate to contact the blood cells with the membrane surface antibodies at a rate that is designated as controlled capillarity. The adhesive assembly of a membrane, already bearing antibody, to the support element results in an unpredictable rate of water absorption thereby increasing the likelihood of non-specific binding of red blood cells or the lysis of red blood cells.

Figure 2:
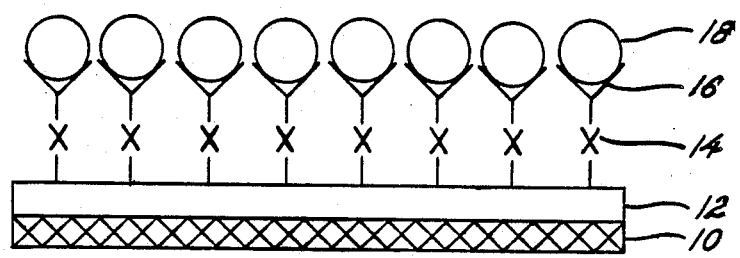
FIG. 2 illustrates the indicator of FIG. 1 after contact with an aqueous liquid containing red blood cells wherein the membrane-surface-interior layer (12) has absorbed liquid and red blood cells (18) are bound to specific type antibody (16).

FIG. 1 illustrates a support (10) in combination with a water permeable membrane (12) a chemical linker (14) and an antibody (16). Any bifunctional chemical or polymer may be used as a linker, or no linker can be used. FIG. 2 illustrates a support (10) adjacent to a membrane (12) which is attached to a linker (14) which in turn is bound to an antibody (16) which is schematically bound to a cell such as a red blood cell. Each cell is bound by multiple antibodies to hold it to the membrane support device. The number of antibodies binding to the cell is that sufficient to retain it during the washing process, preferably 20 or more antibody molecules per cell contact surface area.

Figure 3A:
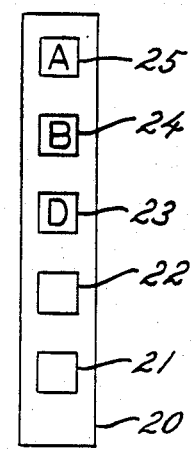
FIGS. 3a and 3b illustrate a blood typing stick containing membrane regions bearing specific antibody against type A, B or D (or $D^u$) blood antigens and the positive and negative controls.
Figure 3B:
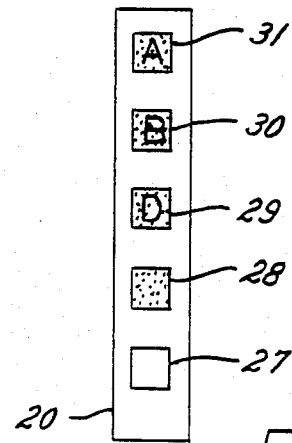
Figure 4:
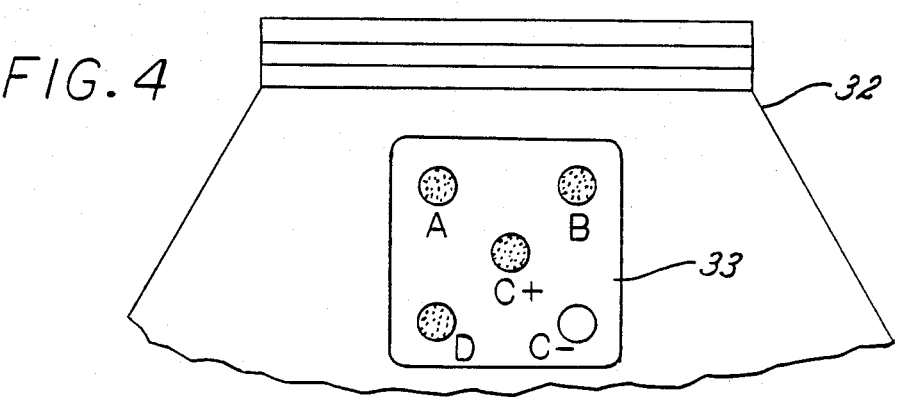
FIG. 4 illustrates a blood bag tag containing membrane-surface-interior regions bearing specific antibody against type A, B, D (or $D^u$) and a control region C+ which contains anti-RBC and region C− containing neutral polymer.

FIGS. 3a, 3b and 4 show a stick (20) or a tag (33) which contains membrane pad regions of the type described with referencre to FIGS. 1 and 2. In one embodiment with dimensions of 6 mm×6 mm 140μ (70% void volume). Three of the membranes, which are indicated at A, B, and D, have surface antibodies specific against blood groups A, B, and D (Rh), respectively. The fourth and fifth pads, the positive control containing anti-RBC antibody and the negative control having non-specific antibodies or non-antibody proteins or other polymers may optionally be present. The supports may be formed on separate membranes and then attached, as by adhesive, to a tag, or the tag itself may be the membrane on which the five pad regions are formed. The tag is preferably white or otherwise light colored to enhance color contrast with the blood cell matrix which is developed on the membrane supports.

FIG. 3a illustrates a stick (20) with the five membrane-pad areas which are an anti-A antibody area (25), an anti-B antibody area (24), and anti-D antibody area (23), a positive control pad bearing antibody against all red blood cells (22), and a negative control (21) bearing neutral protein or protein without affinity for red blood cells. In FIG. 3a all the pad areas are uncolored. In FIG. 3b the pad areas 28, 29, 30 and 31 are speckled indicating the binding of red blood cells. This indicates that the blood type is AB positive and the assay has a positive control (28) and a clear negative control (27) indicating no non-specific absorption of red blood cells. Each pad can be individually adjusted for rate of water absorption to compensate for the varying affinity of the antibody for the red blood cell surface antigen. That is a higher rate of water absorption may be needed to effectively contact lower affinity antibody with cell surface antigens.

The tag is preferably designed for attachment to a blood container to provide a tag on the container identifying the blood type of the contents. In FIG. 4 there is shown a portion of a blood bag (32) having a blood-type identification card, such as a tag (33) adhesively attached to a side of the bag. The particular card shown indicates type B/Rh(+) blood. The method of performing blood group determination assays on the card will be described below.

Soluble antibodies which are specific against cell surface antigens other than the blood-group antigen being tested may also serve to detect cell types according to the method of the invention. One such method is using human leukocytic antigens (HLA) specific antibodies. Methods for preparing such antibodies are well known.

3. Blood-Typing Assay Method

The method of the invention involves, first providing a membrane support of the type described above, constructed for binding specifically and with high affinity to red blood cells having selected cell surface antigens, typically antigens characteristic of blood group A, B, or Rh factor. The membrane must be dry or nearly dry when used to facilitate wicking of the aqueous phase into the membrane.

A sample of the whole blood or blood cells to be typed are added to each membrane in an amount sufficient to cover the membrane, exposing the membrane to the suspended sample cells. Alternatively, a stick or tag bearing the membrane may be immersed in the sample. In a diluted sample containing comparatively few cells, a thicker membrane may be required to absorb a greater quantity of solution to contact the required number of cells with the membrane surface. For example, when a sample has been diluted N times, the associated interior absorbing area must also be increased about N times.

FIG. 3b illustrates the binding of cells to a diagnostic stick bearing a membrane which occurs when the membrane is exposed to the cells in aqueous or whole blood solution. The diagnostic stick in FIG. 3b consists of a backing (20), membrane-wicking region bearing anti-human blood type antibodies (22-25) which are attached to the membrane surface as in FIGS. 1, 2 and 3a.

In FIG. 3b, the bound red blood cells form a dense cell layer (28-31) that is easily detected visually or by scanning devices.

The washed support(s) may be preserved in permanent form by drying, leaving strongly colored dried-matrix areas. If desired, the dried supports (or support regions on a card) can be protected with a spray-on lacquer or the like.

Illustrating the method of the invention as it might be practiced by a blood bank, donor blood is collected in a blood bag,, such as bag (32) (FIG. 4). Blood from the bag is then applied to the support regions of a tag (33). After incubation for 1-3 minutes at room temperature, the card is washed—either by rinsing the tage with a physiological saline solution, or emersing the tag in such a solution, with gentle agitation. The tag now shows strongly colored regions where immunospecific cell binding has occurred, and virtually uncolored regions for the negative regions. In the embodiment illustrated, the assay indicates type AB/Rh(+) blood. The card may be allowed to dry, giving a permanent, easily readable record of blood type. The card can be permanently attached, for example, by stapling, clamping or adhesive backing, to the blood container, in a blood donor setting. In the case of a blood recipient, the card or strip can be attached to the recipient's hospital record or directly to a patient in the form of a bracelet.

Numerous embodiments of the cell detection membrane system are anticipated. Among the mammalian cells anticipated are blood cells, including human and other mammals such as horse, cow, sheep, goat, pig, dog, cat, rabbit, rat and mouse; and eukaryotic tissue culture cell lines. When the cell is detectable due to its own inherent properties, such as red color for red blood cells, then no additional agent is required for detection. However, where the cell is not sufficiently detectable, agents such as dyes, detectably labeled antibodies, or detectably labeled affinity ligands must be used. Among the detectable agents are radioisotopes, enzymes, fluorescent dyes, and electron opaque materials.

Figure 5:
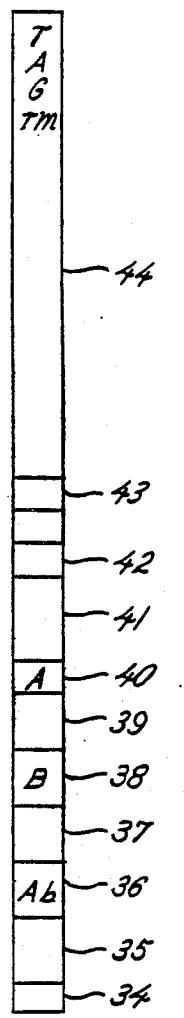
FIG. 5 illustrates a blood typing stick containing color coded membrane regions bearing antibody against A, B, D (or $D^u$), a control region C+ which contains anti-RBC, and a control region C− containing a non-RBC binding blocking polymer.

General embodiments of the cell detection devices are illustrated in FIGS. 1-5, with a specific detector drawn to scale in FIG. 5. The cell detection support device may be any material offering support that does not interfer with detection. Detectors may be in various forms including pads, sticks, tags, bracelets, cards or other embodiments suitable for easy utilization and manufacture.

A specific embodiment, as illustrated to scale in FIG. 5, is a cell detector with membrane surfaces suitable for detecting specific types of red blood cells. The diagnostic strip consists of a support strip (44) suitable for holding by hand for insertion into blood containers. The dimensions anticipated are from 2-6 inches, preferably from 3-5 inches, and most preferably 4.25 inches in length. The width may be from 2-15 mm, preferably 3-9 mm, and most preferably 6 mm. Attached to the support are membrane surfaces containing antibody affinity regions as described in Example I. In this embodiment there are the following distinct regions on the blood typing device: region (34) which is free of membrane to ensure that sediment at the bottom of the solution does not interfere with detection; region (35) containing a membrane with antibody to human D or $D^u$; region (36) with grey lettering "Rh", or with a grey background and lettering of a different color; region (37) containing a membrane with antibody to human B antigen; region (38) with yellow lettering "B" or with a yellow background and lettering of a different color; region (39) containing a membrane with anbibody to human A antigen; region (40) with blue lettering "A" or with a blue background and lettering of a different color; region (41) an open space; region (42) and (43) are membranes for control purposes, one a positive control membrane containing antibody non-specifically binding red blood cells and the other a negative control membrane with a blocking agent such that there is no specific affinity for red blood cells. The order of the membranes on the stick may be changed, the size of the membranes and lettering may be altered, however, the colors are a critical aspect of this embodiment of the invention. This unique design of a diagnostic stick for blood typing embodies the membranes with controlled capillarity and color indicators in compliance with 21 CFR Section 660.28.

Other embodiments of this invention will have indicator regions with a pink "C", a brown "E", an orange "CDE", a lavender "c", or a green "e"; or a similar color background with a different color for the letter.

From the foregoing, it can be appreciated how various objects and features of the invention are met. The blood typing system substantially eliminates the possibility of technical errors due to mix-ups in blood samples or reagents. In the embodiment of the invention illustrated in FIG. 4, blood samples are transferred directly from a blood bag or sample to a card, and the only reagent which is added to the card is a saline wash. Clerical errors are minimized since a visual record of blood type is contained on the card itself.

Unlike other blood typing methods proposed heretofore, the binding reaction in the present invention is easily read visually, i.e., without special spectrophotometer or densitometer equipment and without a requirement for complex interpretation or analysis.

Another important advantage of the invention is that the origianl assay can provide a permanent record of the assay results, so retesting need not be required to confirm blood type.

The following examples are not to be limiting but rather illustrative specific embodiments of the invention.

EXPERIMENTAL

Example I

Preparation of Membrane With Anti-A, Anti-B, or Anti-D Antibody

To a sheet of support or backing material are applied a series of strips of membrane material by the use of double-sided adhesive (Immobilon ™, Millipore Corporation; Adhesives, 3M Corporation). Antibodies against the A, B or D human red blood cell antigens are commercially available (Gamma Biologies, Inc., Houston, TX). These antibodies may be either monoclonal or polyclonal in nature. Following application of the membrane to the support surface there are five steps which are: binding, drying, coating, drying and storing.

In the first step the antibody plus optional inert proteins or polymers such as $\alpha 2$-macroglobulin in phosphate-buffered saline is applied to the membrane. A volume of approximately 10 $\mu l$ of this liquid containing antibody is applied per 6 mm square area of membrane. The antibody solution contains from 0.05 $\mu g$ to 0.5 $\mu g$ of antibody per 10 $\mu l$. The concentration of polymer or protein, when present, is approximately 100 $\mu g$ per 10 $\mu l$. Prior to binding of the antibody the membrane surface had been treated with the necessary coupling reagents. Following the binding of antibody to the membrane there is a 20 min drying period at 27° or for a longer period of time until dry. Once the drying period is completed the next step is coating of the membrane to create the controlled capillarity. To control capillarity a coating solution containing a salt, a surfactant, and a polymer such as a protein or other polymer was applied. One such coating solution containing 20% BSA, the surfactant Tween 20, and sodium chloride in deionized water was used. A 5 μl sample of this coating solution was applied for each 6 mm square area of the membrane.

After the coating step the coated membrane was dried for 20 min at 37° or until dry.

EXAMPLE II

Preparation of Diagnostic Sticks

The sheet bearing the treated membrane was then cut into strips 6 mm wide. These strips could then be stored in a dry, cool or frozen condition until needed. Each membrane area on the strip contained membrane areas 6 mm×6 mm×140μ with an internal volume of 3.5 to 5 μl.

The support sheat bearing the membrane treated with antibody solutions against human antigens A, B and D were cut into strips 6 mm or less in width and 4.25 inches or greater in length. These cut strips were then stored in a dry container containing a desiccant. They may be kept in either a cool or a frozen condition. When needed, the diagnostic strips are removed for use.

EXAMPLE III

Preparation of Diagnostic Tags

Diagnostic tags are prepared by the method similar to that of Example I with the antibody solution and the coating solutions applied to membrane disks attached to a support backing. The support backing has on its opposite side an adhesive backing suitable for application to a container, bracelet or document.

EXAMPLE IV

Test for A, B, AB, O or D Blood Type

Whole blood from A, AB, and O-group donors was obtained from a local blood bank.

Individual membrane diagnostic sticks having membrane surface-bound mouse anti-human blood group A, B, D and RBC prepared as in Example I and Example II were each placed into test tubes bearing whole blood for 60 seconds. The diagnostic stick was then removed and washed with a saline solution (approximately 5–10 ml) or immersed into a saline filled test tube (30–50 ml) for 10–30 seconds. The diagnostic stick was then read.

Visual inspection of the membranes showed:

(a) The A and AB blood types gave a strong color reaction (membrane surface coatings) on disks containing surface-bound anti-A antibodies;

(b) The B and AB blood types gave a strong color reaction on disks containing surface-bound anti-B antibodies.

(c) No appreciable blood cell binding of O-group blood to either anti-A or anti-B membrane was detected.

Table 1 summarizes the results for tests with A+, A−, B+, B−, AB+, AB−, O+ and O− human blood. The red indicating binding. FIGS. 3b and 4 indicate the pattern for AB+.

TABLE 1

| | \multicolumn{8}{c}{Blood Types} |
|---|---|---|---|---|---|---|---|---|
| | A+ | A− | B+ | B− | AB+ | AB− | O+ | O− |
| Anti-A | + | + | − | − | + | + | − | − |
| Anti-B | − | − | + | + | + | + | − | − |
| Anti-D | + | − | + | − | + | − | + | − |
| Anti-RBC (C+) | + | + | + | + | + | + | + | + |
| Neg-Cont (C−) | − | − | − | − | − | − | − | − |

Key:
+ = Red;
− = White

Therefore, the results of Table 1 indicate the detection of mammalian red blood cell type using membrane device having controlled capillarity.

What is claimed is:

1. A blood-typing device for use with a human blood sample containing red blood cells in an aqueous liquid, comprising:

a controlled capillarity membrane having first and second surfaces and a porous interior between said surfaces, said first surface having pore sizes less than about 5 microns and an array of type-specific antibodies capable of immunospecifically binding red blood cells of a selected blood type on said first surface, said porous interior having a base membrane void volume and pore sizes selected to draw said liquid into said interior, wherein said porous interior further comprises a water-soluble polymer coated throughout said porous interior, thereby reducing said base membrane void volume to a reduced void volume while retaining sufficient capillarity to draw liquid into said porous interior, whereby said membrane provides a controlled capillarity so that red blood cells are contacted with said first surface without lysing said cells when said blood sample is applied to said membrane; and a solid support directly attached to said second surface.

2. The device of claim 1, wherein said first surface and said porous interior are composed of different materials.

3. The device of claim 1, wherein said first surface and said porous interior are composed of the same material.

4. The device of claim 3, wherein said solid support comprises a strip from 2–6 inches in length and 2–15 mm in width.

5. The device of claim 1, wherein said porous interior has a capacity sufficient to draw against said membrane a volume of blood sample which contains at least that number of red blood cells necessary to form a visible layer of immunospecifically bound red blood cells on said first surface.

6. The device of claim 5, wherein said membrane has a thickness of at least about 20 microns.

7. The device of claim 1, wherein said membrane comprises polymer fibers composed of polyvinyldifluoride, polytetrafluoroethylene, modified nylon, nitrocellulose, regenerated cellulose, or cellulose.

8. The device of claim 7, wherein said surface is substantially uncharged.

9. The device of claim 1, wherein said antibodies are attached by adsorption of said surface.

10. The device of claim 1, wherein said antibodies are attached covalently to said surface.

11. The device of claim 10, wherein said surface and said interior are formed as a unitary polyvinyldifluoride fiber membrane and said antibodies are attached to said surface by carbodiimidazole coupling.

12. The device of claim 1, wherein said antibodies are selected from the group consisting of anti-A, anti-B, and anti-D antibodies.

13. The device of claim 12, wherein said anti-D antibodies are immunoglobulin M anti-human D monoclonal antibodies effective in binding both D- and $D^u$-type human red blood cells at a surface concentration sufficient to form a visually identifiable cell monolayer on said surface.

14. The device of claim 1, wherein said soluble polymer is polyvinylpyrolidine, polyvinylalcohol, or a protein.

15. The device of claim 1, wherein said soluble polymer is polyvinylpyrolidine.

16. The device of claim 15, wherein said soluble polymer is coated at a rate of from 0.06 mg to 2.3 mg/$\mu$l of interior pore volume.

17. The device of claim 16, wherein said rate is about 0.3 mg polymer/$\mu$l interior pore volume.

18. The device of claim 1, wherein said soluble polymer is coated throughout said porous interior by applying said soluble polymer to said membrane in an aqueous solution.

19. The device of claim 18, wherein said solution further comprises an inorganic salt.

20. The device of claim 18, wherein said solution further comprises a surfactant.

21. The device of claim 1, wherein said base membrane has pore sizes of from 0.65 to 5 $\mu$m.

22. The device of claim 1, wherein said base membrane void volume is about 70%.

23. The device of claim 1, wherein a separate controlled capillarity membrane is attached to a common support means for each blood-type antigen being detected, at least one membrane being selected from the group consisting of:
a first controlled capillarity membrane having attached to its surface an array of anti-A blood type antibodies capable of bonding red blood cells immunospecifically when a type A or AB blood sample is placed against the membrane and the cells are drawn against the membrane by said controlled capillarity of said first membrane;
a second membrane having attached to its surface an array of anti-B blood type antibodies capable of bonding red blood cells immunospecifically when a type A or AB blood sample is placed against the membrane and the cells are drawn against the membrane by said controlled capillarity of said second membrane; and
a third controlled capillary membrane having attached to its surface anti-D blood type antibodies capable of bonding red blood cells immunospecifically when a type $D^u$ blood sample is placed against the membrane and the cells are drawn against the membrane by said controlled capillarity of said third membrane.

24. The device of claim 23, wherein said array of antibodies consists essentially of monoclonal antibodies.

25. The device of claim 23, wherein the anti-D antibody attached to the third membrane is an immunoglobulin M human monoclonal antibody.

26. The device of claim 23, which comprises a further membrane having attached to its membrane surface an array of anti-human red blood cell antibodies capable of binding red blood cells immunospecifically when a blood sample is placed against the membrane and the cells are drawn against the membrane by the controlled capillarity of said fourth membrane or a further membrane having attached to its membrane surface an array of polymer which has no immunospecific binding affinity for red blood cells.

27. The device of claim 23, wherein said antibodies are covalently attached by means of cyanogen bromide to a polyvinyldifluoride membrane.

28. The device of claim 23, wherein said antibodies are attached by adsorption to polytetrafluoroethylene, nitrocellulose, modified nylon, regenerated cellulose, or cellulose.

29. A method of typing red blood cells in a blood sample containing red blood cells in an aqueous liquid, comprising:
contacting said sample with a controlled capillarity membrane having first and second surfaces and porous interior between said surfaces, said first surface having pore sizes less than about 5 microns and an array of type-specific antibodies capable of immunospecifically binding red blood cells in a selected blood type on said first surface, said porous interior having a base membrane void volume and pore sizes selected to draw said liquid into said interior, wherein said porous interior further comprises a water-soluble polymer coated throughout said porous interior, thereby reducing said base membrane void volume while retaining sufficient capillarity to draw liquid into said porous interior, whereby said membrane provides a controlled capillarity so that red blood cells are contacted with said first surface without lysing said cells when said blood sample is applied to said membrane, wherein a solid support is directly attached to said second surface of said membrane, whereby type-specific cells in said sample react immunospecifically with said antibodies to form a monolayer of red blood cells on the membrane when said type-specific cells match said type-specific antibodies;
washing said membrane to remove red blood cells adhering non-specifically to the membrane; and
detecting the presence or absence of said monolayer of red blood cells as an indication of blood type.

30. The method of claim 29, wherein three membranes are provided, a first membrane having anti-A antibodies attached to its surface, a second membrane having anti-B antibodies attached to its surface, and a third membrane having anti-D antibodies attached to its surface.

31. The method of claim 29, wherein said pore sizes are less than 2 microns.

32. The method of claim 31, wherein said pore sizes are about 0.65 microns.

33. The method of claim 29, wherein said sample comprises whole blood diluted N times and said membrane has a thickness of at least about N$\times$20 microns.

* * * * *